United States Patent [19]
Dalton

[11] Patent Number: 5,312,377
[45] Date of Patent: May 17, 1994

[54] TAPERED LUER CONNECTOR

[76] Inventor: Michael J. Dalton, 9432 Monticello Ave., Evanston, Ill. 60203

[21] Appl. No.: 38,273

[22] Filed: Mar. 29, 1993

[51] Int. Cl.⁵ ............................................. A61M 25/00
[52] U.S. Cl. ..................... 604/283; 604/905
[58] Field of Search ............... 604/281, 282, 283, 240, 604/243, 266, 280, 905

[56] References Cited

U.S. PATENT DOCUMENTS

| | | | |
|---|---|---|---|
| 3,434,869 | 3/1969 | Davidson | 604/266 |
| 3,663,288 | 5/1972 | Miller | 604/266 |
| 3,977,403 | 8/1976 | Patel | 604/243 |
| 4,040,421 | 8/1977 | Young | 604/243 |
| 4,294,250 | 10/1981 | Dennehey | 604/905 X |
| 4,360,024 | 11/1982 | Wallace | 604/283 X |
| 4,425,919 | 1/1984 | Alston, Jr. et al. | 604/282 |
| 4,547,193 | 10/1985 | Rydell | 604/282 |
| 4,834,719 | 5/1989 | Arenas | 604/283 |
| 4,969,879 | 11/1990 | Lichte | 604/283 |
| 5,057,092 | 10/1991 | Webster, Jr. | 604/282 |

FOREIGN PATENT DOCUMENTS

| | | | |
|---|---|---|---|
| 2907832 | 9/1980 | Fed. Rep. of Germany | 604/283 |
| 3737665 | 5/1989 | Fed. Rep. of Germany | 604/905 |

*Primary Examiner*—John D. Yasko
*Assistant Examiner*—Frank Wilkens

[57] ABSTRACT

An improvement in the luer taper connectors used to join two fluid conduits, especially in medical applications. Construction of one, the other, or both luer taper members from a soft, resilient, elastomeric material makes it unnecessary to provide a separate threaded luer lock connection, thereby minimizing fluid leaks, thread stripping, cross-threading, infections and thrombus formation associated with rigid and semi-rigid luer taper connectors.

20 Claims, 3 Drawing Sheets

TAPERED LUER CONNECTOR

This invention is in the field of connectors for medical fluid conduits. More specifically, this invention is directed to an improvement in the luer connectors which are typically employed in medical applications.

BACKGROUND

The combination of a male luer connector with a female luer member is widely used in the medical field to connect two fluid conduits end to end. Such male/female sets are employed to join hypodermic needles to syringes and one catheter to another catheter, for example, in order to provide liquid leakproof and mechanically secure connections. A luer connection comprises two distinct elements, a tapered fitting called a "luer-slip" and a subordinate fitting to add additional strength to the connection. The subordinate fitting is generally a "luer-lock" threaded fitting.

The first element, the luer-slip fitting, involves the mating of a conical male nozzle member with a conically-hollowed female socket member. Both members are also hollowed axially to provide communication of the fluid passage between them. The tapers of the two cones are similar, so that, upon slipping the conical male nozzle member into the conically-hollowed female socket member, a frictional seal is achieved which is substantially fluid-tight. The conical tapers of the two members are prescribed by an industry standard, which sets the "luer taper" for such fittings.

The second aspect of a luer taper connection is a subordinate fitting, commonly a threaded connection, between the male and female members which engages to establish an axial force tending to maintain the frictional seal established by the slip fitting. Typically, the male taper member has a coaxial cylindrical skirt which carries internally one component of the threaded connector, while the female taper member carries the other part of the threaded connector externally. The female member may carry a full thread but, more commonly, only an abbreviated thread, in the form of a pair of lugs, is provided. This type of threaded fitting is called a "luer-lock" fitting.

The American National Standard Institute (ANSI) first proposed an American National Standard in 1955 to make luer slip fittings and luer-lock fittings uniform from manufacturer to manufacturer. ANSI MD70.1-1955 was subsequently adopted by the industry. Thus, individual luer fittings for use in medical device applications can make leakproof and mechanically secure connection with any other available individual mating luer fitting. At the time the standard was written the luer taper dimensions required a cone 4.318 mm in diameter at the large end, 3.937 mm in diameter at the small end and 6.350 mm in length, i.e., a 6% taper. In 1955, luer taper fittings were generally made of rigid glass or metal, but semi-rigid thermoplastic fittings of polycarbonate, polypropylene, etc. now predominate.

With reference to semi-rigid luer taper fittings, according to a proposed revision of the 1955 ANSI Standard, the diameter of the small end of the male nozzle member must lie in the range 3.925–4.027 mm, and the minimum length of the nozzle must be 7.500 mm. The diameter at the large end of the female socket member must lie in the range 4.270–4.315 mm, and the minimum depth of the socket must be 7.500 mm. The minimum length of engagement between the male nozzle and the female socket must be 4.050 mm. The Standard also provided requirements for luer-lock fittings, such as the root and crest diameters for the thread, thread pitch and thread angle, but the proposed revision technically applied only to rigid materials. The thread is generally a 1.5 turn, 0.25 inch advance thread of a rather crude design. The most recent Standard is ANSI MD70.1-1992. Reference to the most recent revision of the ANSI Standard should, of course, be made when any new luer taper fitting is being designed.

Whereas the adoption of industry standards for luer-slip and luer-lock fittings has encouraged the use of such connectors, their use is not free from problems. Such problems include fluid leaks due to mismatching of the sealing edges, cross-threading and thread stripping. Whereas the ANSI Standard provides certain dimensions for luer slip fittings, dimensions appear as ranges, and variations between manufacturers within those ranges lead to misfits and leakage. Cross-threading of luer-lock fittings generally occurs when excessive force is applied upon thread engagement, or the members of the fitting are misaligned as the threads are engaged. The result is uneven mechanical force applied to the luer slip fitting and possible leakage thereof. The threads in a luer-lock fitting can be stripped by overzealous application of force upon connection and can lead to misalignment and fluid leakage as the fitting is engaged and disengaged several times, with increasing damage to the threads and slip fit.

Another set of problems arises because the luer taper fittings of metal, glass or thermoplastic, materials believed to be necessary because of the frequent engagement, disengagement and rough handling they receive, are often used to connect soft, resilient elastomeric cathether materials, typically made of silicone rubber. These connections are usually made with an adhesive. Unless great care is taken to smooth the transitions from one material to the other, sharp steps and cavitations are often present in the resultant cathether terminated with a luer taper fitting. These steps and cavitations tend to collect material from the fluid passing through the connected conduits, and the residue is nearly impossible to flush out. This residue is known to be responsible for partial occlusions and infections. The abrupt transition in materials can also be the cause of thrombus formation when blood is transported through the conduits.

It is to the solution of the aforesaid problems that this invention is directed.

SUMMARY OF THE INVENTION

It has now been found that if one, or both, of the rigid or semi-rigid luer members of the prior art is replaced with a soft, resilient, elastomeric luer member it becomes unnecessary to have a subordinate threaded connection to hold the two members of the luer taper connector set together. Absent the threaded connection, the problems with cross-threading and thread stripping disappear. Furthermore, use of the new, soft, resilient, elastomeric luer member can create a secondary seal against fluid leakage, while retaining the axial compression needed to maintain a tight luer slip fit between the male and female luer members.

In addition, since flexible fluid conduit materials, e.g., silicone rubber, and the new, soft, resilient, elastomeric luer members can often be joined without adhesives, the steps and cavitations which can occur where the materials are joined arise less frequently. In fact, it is possible to mold one of the new luer taper fittings and the associated fluid conduit together so that there is no discernable transition between materials.

There are three aspects to this invention. The first aspect of the invention is an improvement in the two-member connector set for joining a pair of fluid conduits by means of luer taper connectors. According to the prior art, the first fluid conduit terminates in a rigid or semi-rigid, axially-hollowed, conical male luer nozzle member equipped with one part of a two-part mating thread means. The second fluid conduit terminates in a rigid or semi-rigid, axially and conically-hollowed, complementary female luer socket equipped with the other part of the thread means. The improvement comprises substituting at least one soft, resilient, elastomeric luer member carrying neither part of the thread means for either the male or the female luer member of the prior art, or for both members of the prior art.

Thus, this invention provides several distinct sets for joining fluid conduits by means of luer taper connectors. That is, a male fitting of the prior art coupled with a female fitting of this invention, or a prior art female fitting coupled with a male fitting of this invention, or a male fitting of this invention coupled with a female fitting of this invention.

According to a second aspect of the invention, an improved female luer member is provided by substituting for a rigid or semi-rigid, axially and conically-hollowed female luer socket member of the prior art, which carries one part of a two-part thread means externally on the socket wall, a soft, resilient, elastomeric female luer member which carries neither part of the thread means, but n which the socket wall is sized externally to interfere with and conform itself to that part of the thread means carried by the male luer member when the members are joined.

A third aspect of the invention provides an improved male luer member by substituting for a rigid or semi-rigid, axially-hollowed, conical male nozzle member of the prior art, having a coaxial cylindrical skirt which carries internally one part of a two-part thread means, a soft, resilient, elastomeric male luer member which carries neither part of the thread means, but in which the skirt is sized internally to interfere with and conform itself to the thread means carried by the female luer member when the members are joined.

The invention, as well as the manner and means by which it can be carried out will become clear by reference to the drawings which accompany this specification and to the detailed description which follows.

DETAILED DESCRIPTION

Figure 1:
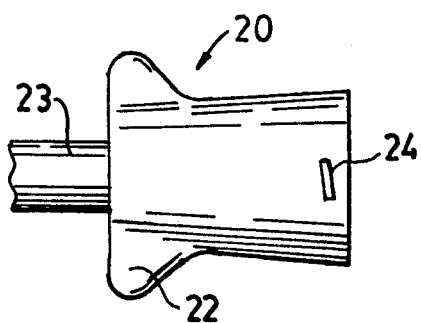
FIG. 1 is a side view of a female luer fitting of the prior art.

Each of the two-member luer taper connector sets of this invention is characterized as including at least one soft, resilient and elastomeric luer member; the individual male and female luer members of this invention are similarly characterized. On the other hand, the luer taper connector sets and individual luer members of the prior art are rigid or semi-rigid. This is a key distinction.

The rigid materials employed in the prior art are metal or glass, having characteristics such as being hard and brittle. More recently, thermoplastics, such as polypropylene, polycarbonate, rigid PVC and ABS have been employed in luer taper fittings. One characteristic of polymeric thermoplastics typically used in semi-rigid luer taper fittings is that the glass transition temperatures generally are higher than about 25 deg. C., which is the approximate temperature at which the fittings are used.

In contrast, the soft, resilient, elastomeric materials employed in the luer taper fittings of this invention are more properly classified as rubbers, rather than thermoplastics. The polymeric materials useful in this invention typically have glass transition temperatures lower than about 25 deg. C. Moreover, the rubbers useful in this invention, vulcanized or otherwise cured as appropriate, have a durometer hardness in the range of about Shore A60 to about Shore A90, which is quite soft. In addition, the useful rubbers are resilient, exhibiting a rebound of at least about 50%, and they are elastomeric, with elongation at the break of at least about 100%. All the aforesaid properties are referred to at about 25 deg. C.

There is a wide range of soft, resilient, elastomeric materials which meet the functional requirements and can be employed in the luer members of this invention. These materials include: polyisoprene, poly(styrene-co-butadiene), polyisobutylene, polychloroprene, poly(-butadiene-co-acrylonitrile), polysulfide, polyurethane, polyacrylate, polysiloxane and poly(fluorovinylsilane). However, there is one additional qualification the material must meet. It must be medically acceptable for the intended use. Among the recited materials, polyurethane, polyacrylate and polysiloxane rubbers are preferred, and polysiloxane, or silicone, rubbers are especially attractive. Catheters and other fluid conduits are often made of silicone rubber, permitting the conduit and the luer taper fitting to be molded together or at least joined smoothly. Readily available silicone rubber products which can be advantageously employed in the invention are SILASTIC brand silicone elastomer products and materials, which can be obtained from Dow-Corning Corporation, Midland, Mich. More specifically, copolymers of dimethyl and methylvinyl siloxane, which may contain silica reinforcement, can be used, an example being Dow Corning SILASTIC Q7-4790 Medical Grade ETR Elastomer, a two-part product.

The luer taper fittings employed in this invention each comprise a single piece which can be produced by conventional rubber molding techniques, such as transfer compression molding or injection molding. These techniques can be employed with the SILASTIC brand elastomers, for example.

Figure 2:
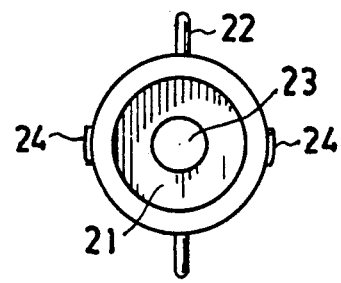
FIG. 2 is an end view of the fitting of FIG. 1.
Figure 11:
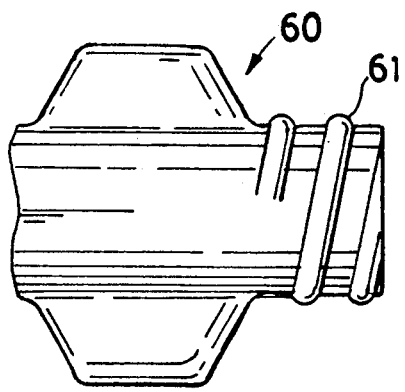
FIG. 11 is a side view of a prior art female luer member which is not of this invention.

With reference now to the Figures, FIGS. 1 and 2 illustrate a typical female luer member of the prior art. Rigid or semi-rigid female luer socket member 20 is axially and conically hollowed, the external wall of the socket carrying one part of a two-part thread means, in this case lugs 24. Wings 22 are provided to assist in rotating the member to engage lugs 24 with mating thread means associated with a complementary male luer member. The conical male nozzle of the mating luer member creates a slip fit against luer taper 21 of the female luer member. Fluid outlet 23 is the fluid conduit attached to the luer fitting. An alternative luer member 60 is shown in FIG. 11. In this case the female luer member carries a full thread 61 on the outside of socket wall 62.

Figure 4:
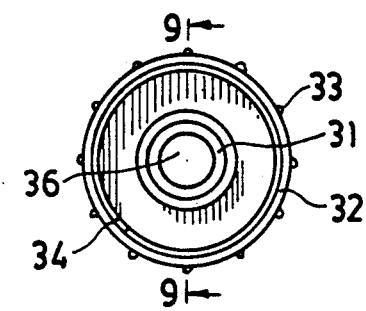
FIG. 4 is an end view of the fitting of FIG. 3.
Figure 3:
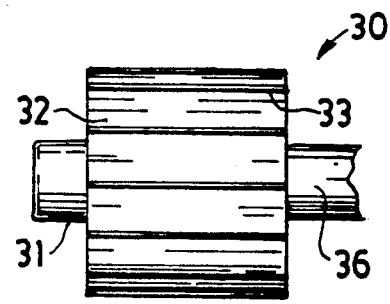
FIG. 3 is a side view of a male luer fitting of the prior art.
Figure 9:
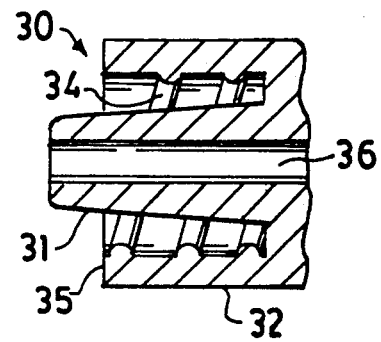
FIG. 9 is a cross-sectional view taken along line 9—9 in FIG. 4.

FIGS. 3 and 4 illustrate a typical male luer member of the prior art. FIG. 9 shows the fitting in cross-section. Rigid or semi-rigid luer member 30 has an axially-hollowed nozzle with luer taper 31. The conical nozzle member is encircled by coaxial cylindrical skirt 32. The skirt may have a knurl 33 externally. Internally, the skirt 32 carries one part 34 of a two-part thread means. Axial hollow 36 is in communication with the fluid conduit.

Figure 5:
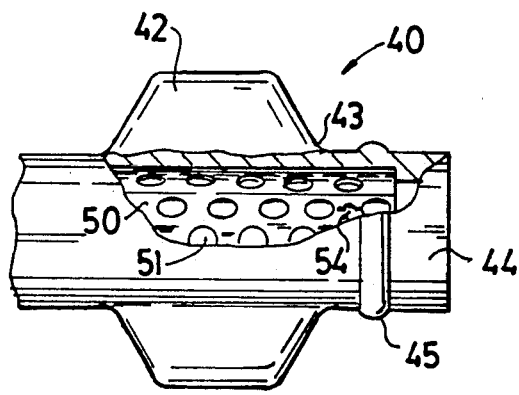
FIG. 5 is a side view of one embodiment of a female luer member of this invention, including several optional elements and a portion cut away.
Figure 6:
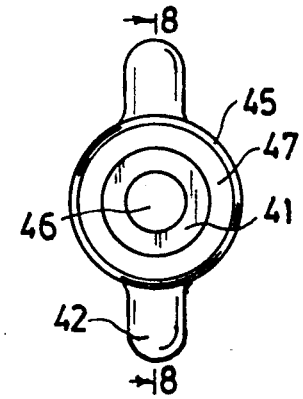
FIG. 6 is an end view of the luer member of FIG. 5.
Figure 8:
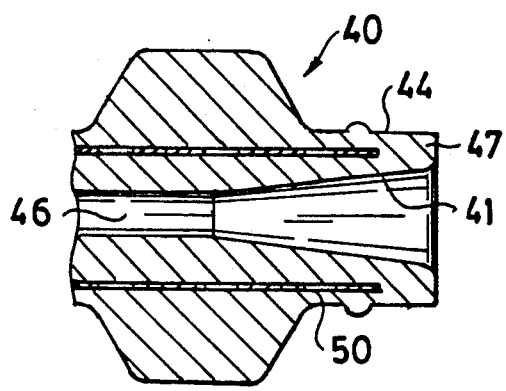
FIG. 8 is a cross-sectional view taken along line 8—8 in FIG. 6.

FIGS. 5, 6 and 8 together illustrate a female luer member of this invention having several optional, but preferred, features. Soft, resilient, elastomeric female luer socket member 40 is axially and conically hollowed to provide female luer taper 41 and a lead 46 to a fluid conduit. Socket wall 47 has an external thread-receiving periphery 44 which does not carry thread means per se but is sized externally to interfere with and conform itself to mating means carried by a male luer member when the members are joined. Circumferential rib 45 is an optional but preferred feature which is especially useful when the fitting is mated with a complementary male member, as will become apparent hereinafter. The fitting may be equipped with rotational wings 42 to assist in gripping it.

Figure 7:
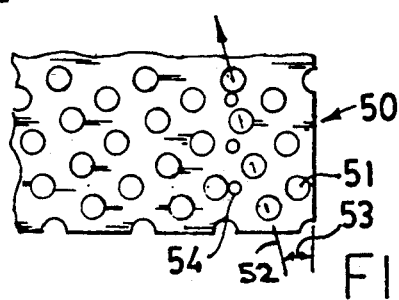
FIG. 7 is the horizontal plan of the optional stiffening insert employed in luer members of this invention, including unrequired but preferred elements.

Female luer member 40 is optionally equipped with a cylindrical stiffening insert 50 which can be encapsulated in silicone by a process called insert molding the fitting, which is well known in the art. The insert is conveniently fabricated from very thin (e.g., about 0.01 in. to about 0.02 in.) metal or thermoplastic. Although not required, the insert is preferably perforated, the perforations 51 being arranged along thread path 52 (see FIG. 7), angle 53 being the thread angle. Another optional feature of the stiffening insert is the protrusions 54 which assist in anchoring the thread of a mating male luer fitting.

Figure 12:
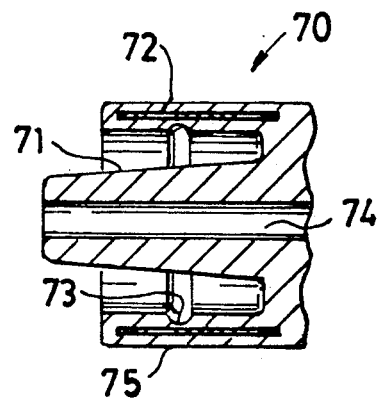
FIG. 12 is a cross-sectional view of one embodiment of a male luer member of this invention, including optional elements.

FIG. 12 shows a soft, resilient, elastomeric male luer nozzle member of this invention. Externally, the male luer nozzle member will closely resemble FIG. 3. Male luer member 70 has a nozzle with luer taper 71 and is axially-hollowed to provide lead 74 to the fluid conduit. The nozzle is encircled by coaxial cylindrical skirt 75.

In contrast to the prior art, skirt 75 does not carry thread means per se but is sized internally to interfere with and conform itself to mating means carried by a female luer member when the members are joined. Cylindrical stiffening insert 72 is optional and is equivalent to stiffening insert 50 described in the preceding paragraph and further illustrated in FIG. 7. Circumferential groove 73 is also an optional feature which is preferably present and adapts a male luer member of this invention which is so equipped to effectively mate with a female luer member of this invention carrying a complementary circumferential rib, e.g., rib 45 in FIG. 5.

Figure 10:
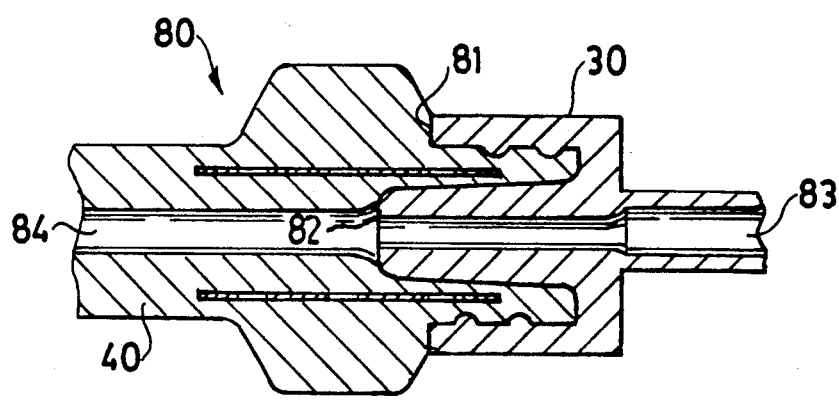
FIG. 10 is a cross-sectional view of one embodiment of a luer taper connection set of this invention produced by mating the luer members shown in FIGS. 8 and 9.

In producing one two-member set of luer taper connectors according to this invention, a female luer member 40 of this invention, shown in FIGS. 5, 6 and 8, can be joined with a male luer member 30 of the prior art, shown in 12. The result is the set of this invention illustrated in FIG. 10. Set 80 includes male luer member 30 coupled with female luer member 40. Leading edge 35 of male member 30 makes a seal 81 against shoulder 43 of female member 40. The thread-receiving periphery 44 conforms itself to the internal thread 34 of the male member by virtue of its sizing and soft, resilient, elastomeric character. The luer taper 41 is deformed by the male luer taper 31 to provide a substantially smooth transition from one member to the other. Fluid conduit leads 83 and 84 lead away from the set.

Figure 13:
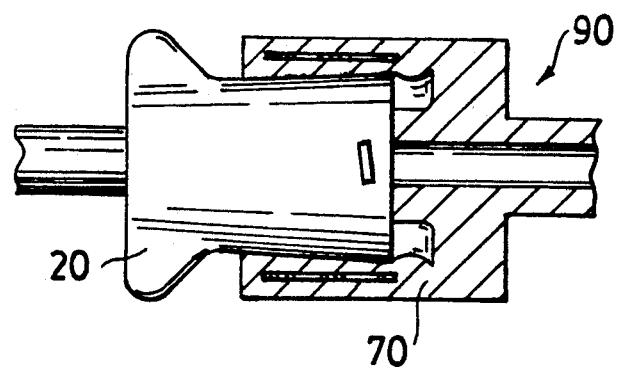
FIG. 13 is a view, partially in section, showing another luer taper connection set of this invention produced by mating the luer members shown in FIGS. 1 and 12.

Another two-member set of this invention is illustrated in FIG. 13 in which male luer member 70 of this invention, shown in FIG. 12, is united with female member 20 of the prior art, shown in FIG. 1, producing set 90. It will be evident that male luer member 70 of this invention can also be mated with a female luer member 60 of the prior art shown in FIG. 11, skirt 75 conforming itself to the full thread 61 by virtue of its sizing and its soft, resilient, elastomeric character.

Figure 14:
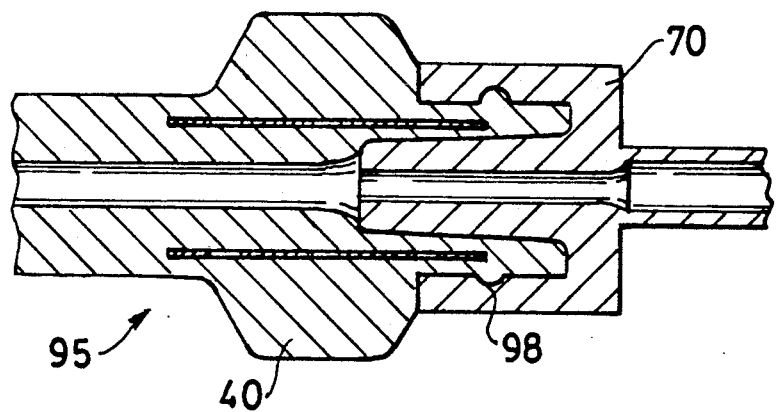
FIG. 14 is a cross sectional view, like FIG. 10, showing still another luer taper connection set of this invention produced by mating the luer members shown in FIGS. 8 and 12.

A third two-member set of this invention is shown in FIG. 14 wherein set 95 is produced by joining a female luer member of this invention 40, illustrated in FIGS. 5, 6 and 8 with a male member of this invention 70, illustrated in FIG. 12, but in which the optional stiffening insert 72 has been omitted. The lock 96 has been created by mating the optional circumferential rib 45 and optional circumferential groove 73. It will be evident the rib and groove can be switched between the members.

There are a number of other variants of this invention which are not specifically illustrated herein but which are clearly within the contemplation and spirit of the invention. Thus, the intended scope of this invention is set forth in the following claims.

I claim:

1. A two-member set for joining two fluid conduits comprising a first fluid conduit which terminates in an axially-hollowed, conical male luer nozzle member encircled by a coaxial cylindrical skirt which carries internally one part of a two-part mating means, and a second fluid conduit which terminates in an axially and conically-hollowed, complementary female luer socket member having a socket wall which carries externally the other part of said two-part mating means, at least one of said members being thread-less and comprised of soft, resilient, elastomeric rubber having a glass transition temperature lower than about 25 degrees C, whereby said soft, resilient, elastomeric member inherently conforms itself, when the members are joined, to the mating means carried by the other member of the set.

2. The set of claim 1 wherein the male member is constructed of soft, resilient, elastomeric rubber, and the skirt is sized internally to interfere with and conform to thread means carried by the female member when the members are joined.

3. The set of claim 1 wherein the female member is constructed of soft, resilient, elastomeric rubber, and the socket wall is sized externally to interfere with and conform to thread means carried by the male member when the members are joined.

4. The set of claim 3 further comprising a tubular stiffening insert embedded in said socket wall.

5. The set of claim 1 wherein the male member is constructed of soft, resilient, elastomeric rubber and the cylindrical skirt is sized internally to interfere with and conform to the female member which is also constructed of soft, resilient, elastomeric rubber and the socket wall is sized externally to interfere with and conform to the male member when the members are joined.

6. The set of claim 5 further comprising a circumferential rib located internally on said skirt, together with a mating circumferential groove located externally on said socket wall, whereby mating said members anchors said rib in said groove.

7. A female luer socket member comprised of soft, resilient, elastomeric rubber having a glass transition temperature lower than about 25 degrees C and an axially and conically-hollowed socket having a threadless socket wall interference-sized externally, whereby said female luer member conforms itself to thread means carried by a complementary male luer member when the members are joined.

8. The female luer member of claim 7 further comprising a tubular stiffening insert embedded in said socket wall.

9. The female luer member of claim 7 further comprising a perforated tubular stiffening insert embedded in said socket wall wherein said perforations are aligned to follow the pitch of said thread means.

10. The female luer member of claim 7 further comprising a circumferential rib located externally on said socket wall.

11. A male luer nozzle member comprised of soft, resilient, elastomeric rubber having a glass transition temperature lower than about 25 degrees C and an axially-hollowed conical nozzle encircled by a threadless coaxial cylindrical skirt interference-sized internally, whereby said male luer member conforms itself to thread means carried by a complementary female luer member when the members are joined.

12. The male luer member of claim 11 further comprising a tubular stiffening insert embedded in said cylindrical skirt.

13. The male luer member of claim 11 further comprising a perforated stiffening insert embedded in said cylindrical skirt wherein said perforations are aligned to follow the pitch of said thread.

14. The male luer member of claim 11 further comprising a circumferential rib located internally on said skirt.

15. The set of claim 5 further comprising a circumferential groove located internally on said skirt, together with a mating circumferential rib located externally on said socket wall, whereby mating said members anchors said rib in said groove.

16. The female luer member of claim 7 further comprising a circumferential groove located externally on said socket wall.

17. The male luer member of claim 11 further comprising a circumferential groove located internally on said skirt.

18. The set of claim 1 wherein the rubber has a durometer hardness in the range of about Shore A60 to about Shore A90, exhibits a rebound of at least about 50% and elongation at the break of at least about 100%.

19. The female luer member of claim 7 wherein the rubber has a durometer hardness in the range of about Shore A60 to about Shore A90, exhibits a rebound of at least about 50% and elongation at the break of at least about 100%.

20. The male luer member of claim 11 wherein the rubber has a durometer hardness in the range of about Shore A60 to about Shore A90, exhibits a rebound of at least about 50% and elongation at the break of at least about 100%.

* * * * *